US00PP28489P2

(12) United States Plant Patent
Klemm et al.

(10) Patent No.: US PP28,489 P2
(45) Date of Patent: Oct. 3, 2017

(54) ***PELARGONIUM* PLANT NAMED 'KLEPS15379'**

(50) Latin Name: *Pelargonium grandiflorum*
Varietal Denomination: KLEPS15379

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 73 days.

(21) Appl. No.: 14/998,955

(22) Filed: Mar. 9, 2016

(51) Int. Cl.
*A01H 5/02* (2006.01)

(52) U.S. Cl.
USPC ..... Plt./324

(58) Field of Classification Search
USPC ..... Plt./324
See application file for complete search history.

*Primary Examiner* — Anne Grunberg
(74) *Attorney, Agent, or Firm* — Bethany R. Roahrig; Barbara Campbell; Cochran Freund & Young, LLC

(57) ABSTRACT

A new *pelargonium* plant particularly distinguished by light lavender flowers with a large purple eye and an upright growth habit, is disclosed.

1 Drawing Sheet

Genus and species: *Pelargonium grandiflorum.*
Variety denomination: 'KLEPS15379'.

BACKGROUND OF THE NEW PLANT

The present invention comprises a new and distinct variety of *pelargonium*, botanically known as *Pelargonium grandiflorum* and hereinafter referred to by the variety name 'KLEPS15379'. 'KLEPS15379' originated from a cross-combination in August 2010 in Stuttgart, Germany between the female *pelargonium* variety 'PS-2009-0001' (unpatented) and the proprietary male *pelargonium* variety 'PSH-2009-C-Bright Red' (unpatented).

Seeds from the cross-combination were obtained and sown and plants were grown for evaluation. A single plant was selected in June 2011 and subsequently named 'KLEPS15379'. In August 2011 'KLEPS15379' was first vegetatively propagated in Stuttgart, Germany by vegetative cuttings from stems and branchings. 'KLEPS15379' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Light lavender with a large purple eye flower color; and
2. An upright growth habit.

DESCRIPTION OF THE PHOTOGRAPH

This new *pelargonium* plant is illustrated by the accompanying photograph which shows an overall view of the plant. The photograph is of an approximately ten-week-old plant grown in Stuttgart, Germany under greenhouse conditions in April 2014. The colors shown are as true as can be reasonably obtained by conventional photographic procedures.

DESCRIPTION OF THE NEW VARIETY

The following detailed descriptions set forth the distinctive characteristics of 'KLEPS15379'. The data which define these characteristics were collected from asexual reproductions carried out in Stuttgart, Germany. Data was collected on plants grown 5-months after planting in Stuttgart, Germany under a glass covered greenhouse in July 2015. Color references are to The R.H.S. Colour Chart of The Royal Horticultural Society of London (R.H.S.), 5$^{th}$ edition (2007).

Classification:
- *Family.*—Geraniaceae.
- *Botanical.*—*Pelargonium grandiflorum.*
- *Common.*—*Pelargonium.*
- *Designation.*—'KLEPS15379'.

Parentage:
- *Female parent.*—The female *pelargonium* variety 'PS-2009-0001' (unpatented).
- *Male parent.*—The proprietary male *pelargonium* variety 'PSH-2009-C-Bright Red' (unpatented).

Plant:
- *Form.*—Bushy and round.
- *Habit.*—Upright.
- *Height.*—24.0 cm.
- *Spread.*—23.0 cm.
- *Natural flowering season.*—Spring to autumn.
- *Propagation type.*—Vegetative cuttings.
- *Time to produce a finished flowering plant.*—4 to 5 months.
- *Time to initiate and develop roots.*—25 days.
- *Root description.*—White and fine (RHS 27D).

Stems:
- *Quantity of stems per plant.*—5.
- *Color.*—RHS 137B.
- *Surface texture.*—Moderately pubescent.
- *Stem form.*—Round.
- *Diameter.*—0.6 cm.
- *Length.*—5.0 cm to 7.0 cm.

*Internode length.*—1.0 cm to 1.5 cm.
*Anthocyanin.*—Absent.

Leaves:
*Arrangement.*—Alternate.
*Shape.*—Cordate.
*Apex.*—Acute.
*Base.*—Open.
*Margin.*—Crenate.
*Surface texture.*—Upper surface: Smooth, sparsely pubescent. Lower surface: Smooth.
*Length.*—4.0 cm.
*Width.*—5.0 cm.
*Color.*—Upper surface: RHS 137B. Lower surface: RHS 137C.
*Petiole.*—Length: 4.0 cm to 7.0 cm. Diameter: 0.15 cm. Color: RHS 137A. Strength: Medium.
*Venation pattern.*—Palmate.
*Venation color.*—Upper surface: RHS 137B. Lower surface: RHS 137D.

Inflorescence:
*Lastingness of flowers on the plant.*—6 to 8 days.
*Umbels.*—Quantity of umbels per plant: 5. Length: 4.0 cm to 5.0 cm. Diameter: 5.0 cm.
*Individual florets of the umbel.*—Quantity of florets per umbel: 3 to 6. Depth: 2.5 cm. Diameter: 3.5 cm.
*Fragrance.*—Absent.

Flower buds:
*Cluster shape.*—Round.
*Cluster size.*—Length: 1.0 cm to 1.5 cm. Width: 2.0 cm.
*Surface texture.*—Moderately pubescent.
*Bud.*—Height: 0.8 cm to 1.1 cm. Width: 0.6 cm. Shape: Elliptic. Apex: Acute. Base: Obtuse. Margin: Smooth. Color: RHS 137C.

Petals:
*Quantity per flower.*—5 to 6.
*Shape.*—Drop-shaped.
*Apex.*—Entire.
*Base.*—Obtuse.
*Margin.*—Entire.
*Length.*—3.5 cm.
*Width.*—1.0 cm to 1.8 cm.
*Surface texture.*—Upper surface: Smooth. Lower surface: Smooth.
*Color of lobes.*—Upper lobes: Upper surface: RHS 76C with eye of RHS N79C. Lower surface: RHS 76D and RHS 71C. Lower lobes: Upper surface: RHS 76C with eye of RHS N79C. Lower surface: RHS 76D and RHS N79D.

Sepals:
*Number per flower.*—5.
*Shape.*—V-shaped.
*Apex.*—Cuspidate.
*Base.*—Obtuse.
*Margin.*—Entire.
*Surface texture.*—Upper surface: Smooth. Lower surface: Moderately pubescent.
*Color.*—Upper surface: RHS 137C. Lower surface: RHS 137D.
*Length.*—1.2 cm.
*Width.*—0.5 cm.

Pedicel:
*Length.*—1.5 cm to 1.8 cm.
*Diameter.*—0.1 cm.
*Color.*—RHS 137C.
*Surface texture.*—Moderately pubescent.
*Strength.*—Medium.

Peduncle:
*Length.*—4.0 cm to 7.0 cm.
*Diameter.*—0.1 cm.
*Color.*—RHS 137B.
*Surface texture.*—Moderately pubescent.
*Strength.*—Medium.

Reproductive organs:
*Stamens.*—Quantity of stamens per flower: Greater than 5. Anther length: 0.2 cm. Filament length: 0.8 cm. Filament color: RHS 62C. Pollen amount: Moderate. Pollen color: RHS 62B.
*Pistils.*—Number: 1. Stigma color: RHS 63A. Style length: 1.3 cm. Style color: RHS 63B. Ovary arrangement: Central. Ovary color: RHS 138D. Ovary diameter: 0.1 cm. Ovary length: 0.2 cm.

Fruit and seed set: None observed.

Disease and pest/insect resistance: None observed.

COMPARISON WITH PARENTAL LINES AND KNOWN VARIETY

'KLEPS15379' is distinguished from its parents as described in Table 1:

TABLE 1

Comparison with Parental Lines

| Characteristic | 'KLEPS15379' | Female parent 'PS-2009-0001' | Male Parent 'PSH-2009-C-Bright Red" |
|---|---|---|---|
| Flower size | Medium | Small | Medium |
| Flower color | Light lavender with large purple eye | Lavender with a purple eye | Red with a purple eye |

'KLEPS15379' can be compared to the commercial variety CANDY FLOWERS Bicolour Regal Geranium, also known as 'Cambi' (U.S. Plant Pat. No. 20,426). Differences between the two varieties are described in Table 2:

TABLE 2

Comparison with Similar Variety

| Characteristic | 'KLEPS15379' | Commercial line CANDY FLOWERS Bicolour Regal Geranium |
|---|---|---|
| Plant habit | Upright | Upright, outwardly spreading and mounded |
| Plant spread or width | 23.0 cm | 43.0 cm |
| Flower longevity | 6 to 8 days | About 2 weeks |

We claim:

1. A new and distinct variety of *pelargonium* plant named 'KLEPS15379' as illustrated and described herein.

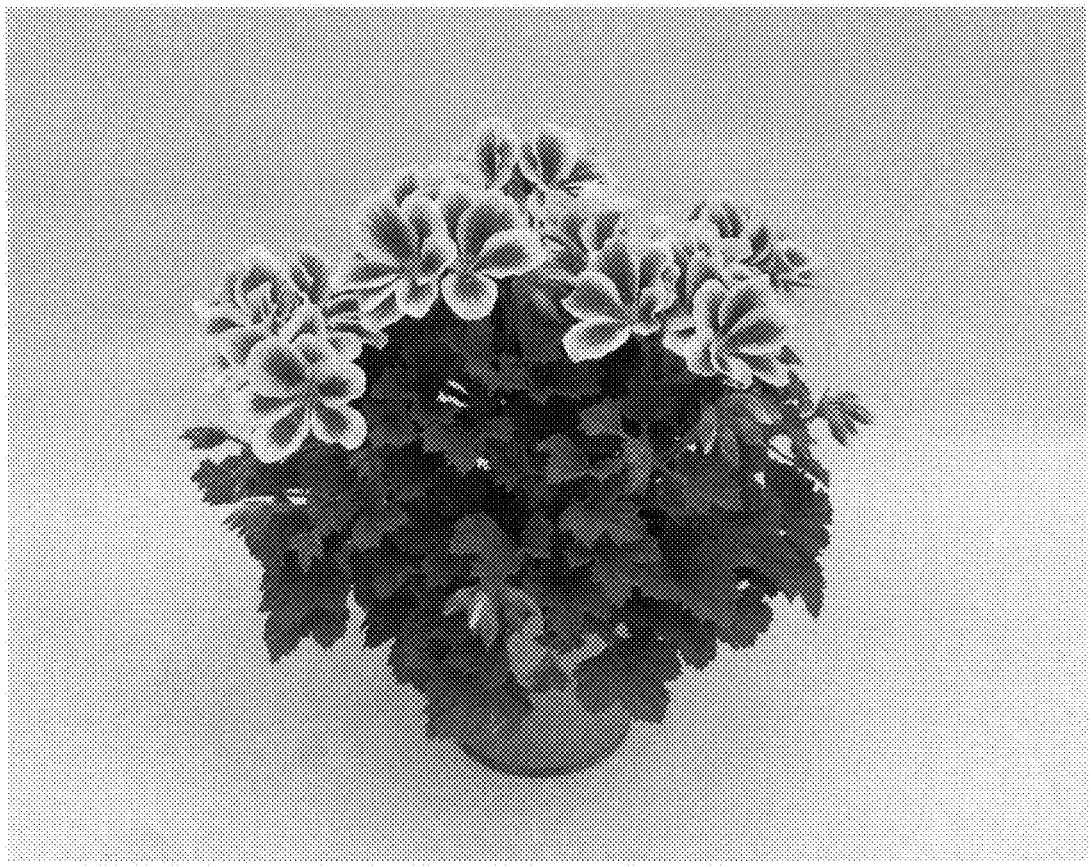

* * * * *